US008871818B2

(12) United States Patent
Tsuji et al.

(10) Patent No.: US 8,871,818 B2
(45) Date of Patent: Oct. 28, 2014

(54) GASTROINTESTINAL ABSORPTION ENHANCER MEDIATED BY PROTON-COUPLED TRANSPORTER AND ITS PREPARING METHOD

(75) Inventors: Akira Tsuji, Kanazawa (JP); Ikumi Tamai, Kanazawa (JP); Yoshimichi Sai, Kanazawa (JP); Masaaki Odomi, Tokushima (JP); Hidekazu Toyobuku, Tokushima (JP)

(73) Assignees: Otsuka Pharmaceutical Co., Ltd., Tokyo (JP); Tsuji Akira, Ishikawa (JP)

( * ) Notice: Subject to any disclaimer, the term of this patent is extended or adjusted under 35 U.S.C. 154(b) by 115 days.

(21) Appl. No.: 12/254,905

(22) Filed: Oct. 21, 2008

(65) Prior Publication Data

US 2009/0048350 A1 Feb. 19, 2009

Related U.S. Application Data

(62) Division of application No. 11/971,243, filed on Jan. 9, 2008, which is a division of application No. 10/541,019, filed as application No. PCT/JP2004/000070 on Jan. 8, 2004.

(30) Foreign Application Priority Data

Jan. 14, 2003 (JP) ................. 2003-006005

(51) Int. Cl.
*A61K 47/30* (2006.01)
*A61K 9/14* (2006.01)
*A61K 47/00* (2006.01)
*A61K 38/00* (2006.01)
*A61K 38/55* (2006.01)
*A61K 47/32* (2006.01)

(52) U.S. Cl.
CPC .................................... *A61K 47/32* (2013.01)
USPC ........ 514/772.3; 514/773; 514/16.3; 514/3.7; 514/19.3; 424/484; 424/486; 424/487

(58) Field of Classification Search
None
See application file for complete search history.

(56) References Cited

U.S. PATENT DOCUMENTS

| | | | |
|---|---|---|---|
| 5,158,777 A | 10/1992 | Abramowitz et al. | |
| 5,322,697 A | 6/1994 | Meyer | |
| 5,651,985 A * | 7/1997 | Penners et al. | ................ 424/469 |
| 5,654,004 A | 8/1997 | Okayama et al. | |
| 5,728,402 A * | 3/1998 | Chen et al. | .................... 424/481 |
| 5,753,253 A | 5/1998 | Meyer | |
| 6,555,124 B1 | 4/2003 | Kolter et al. | |
| 2001/0026807 A1 | 10/2001 | Watts | |
| 2002/0142042 A1 | 10/2002 | Mumper et al. | |

FOREIGN PATENT DOCUMENTS

| | | | |
|---|---|---|---|
| CN | 1226834 | 8/1999 | |
| EP | 0 612 520 | * 8/1994 | ............... A61K 9/00 |
| EP | 612520 | 8/1994 | |
| EP | 0612520 | * 8/1994 | ............... A61K 9/00 |
| EP | 0 800 828 A1 | 10/1997 | |
| JP | 7-507546 T | 8/1995 | |
| JP | 9-188617 A | 7/1997 | |
| JP | 2000-086535 A | 3/2000 | |
| WO | 91/16042 | 10/1991 | |
| WO | 9805360 | 12/1998 | |
| WO | 00/32172 | 6/2000 | |
| WO | WO 00/76479 A1 | 12/2000 | |
| WO | 03/000285 | 1/2003 | |

OTHER PUBLICATIONS

Nozawa et al.; J. of Pharm. Sciences, vol. 92, No. 11, pp. 2208-2216 (Nov. 11, 2003).*
Tsuji et al. "Carrier-Mediated Intestinal Transport of Drugs"; Pharm Res; vol. 13, No. 7 (1996).*
Arai et al., An acidic change in the gastric and jejunal juice of chronic pancreatitis patients, Suizo, 11 (3), pp. 223-230 (1996).
Summary of the 120th meeting of Pharmaceutical Society of Japan, Structure correlation in kinetics of a drug in vivo, (No. 49 report) vol. 4, pp. 51 No. 30 [PD] Dec. 14, 2000.
T. Hoshi et al., Basic Properties of Intestinal Transport of Peptides, Studies on Essential Amino Acids, No. 144, pp. 3-5 (1995).
European Search Report dated Apr. 28, 2011, issued in corresponding European Appln. No. 04700783.6.
Leroux J. C. et al, "Pharmacokinetics of a novel HIV-1 protease inhibitor incorporated into biodegradable or enteric nanoparticles following intravenous and oral administration to mice", Journal of Pharmaceutical Sciences, American Pharmaceutical Association, Washington, US, vol. 84, No. 12, Dec. 1, 1995, pp. 1387-1391, XP008049902.
Tamai I., et al., "Functional expression of intestinal dipeptide/beta-lactam antibiotic transporter in *Xenopus laevis* oocytes", Biochemical Pharmacology, Pergamon, Oxford, GB, vol. 48, No. 5, Aug. 30, 1994, pp. 881-888, XP025552891.
Tamai, I., et al., "Carrier-mediated approaches for oral drug delivery", Advanced Drug Delivery Reviews, vol. 20, No. 1, Jul. 12, 1996, pp. 5-32, XP002633372.
Tsuji, A. et al, "Evidence for a carrier-mediated transport system in the small intestine available for FK-089 A new cephalosporin antibiotic without an amino group", The Journal of Antibiotics, vol. 39, No. 11, Nov. 1, 1986, pp. 1592-1597., XP002633371.
Office Action dated Jul. 2, 2013 on copending U.S. Appl. No. 10/541,019.
Sakamoto et al, *J. Antibiot.*, 38:496-504 (1985).

(Continued)

*Primary Examiner* — Jeffrey T Palenik
(74) *Attorney, Agent, or Firm* — Sughrue Mion, PLLC

(57) ABSTRACT

The present invention provides a pharmaceutical preparation that can improve absorption of a pharmaceutical compound in the gastrointestinal tract and that provides, through oral administration or like method, a blood concentration from which sufficient remedial effects can be expected, and a method for producing such a preparation. The invention is directed to a pharmaceutical preparation exhibiting excellent gastrointestinal absorbability comprising a compound recognized by a proton-coupled transporter and a pH-sensitive polymer in an amount sufficient for the gastrointestinal tract to acquire a pH at which the proton-coupled transporter optimally absorbs the compound into a cell.

4 Claims, 6 Drawing Sheets

(56) References Cited

OTHER PUBLICATIONS

Kelly et al, *Clin. Pharmacokinet.*, 19:177-196 (1990).
Swenson et al, *Adv. Drug Del. Rev.*, 8:39-92 (1992).
Kompella et al, *Adv. Drug Del. Rev.*, 46:211-245 (2001).
Hayakawa et al, *Pharm. Res.*, 9:535-540 (1992).
Zhou et al, *J. Control Rel.*, 29:239-252 (1994).
Terao et al, *J. Pharm. Pharmacol.*, 53:433-440 (2000).
Tsuji et al, *Pharm. Res.*, 11:30-37 (1994).
Davies et al, *Pharm. Res.*, 10:1093-1095 (1993).
Barr et al, *J. Pharm. Sci.*, 59:154-163 (1970).
Fei et al, *Nature*, 368:563-566 (1994).
Bradford, *Analytical Biochemistry*, 72:248-254 (1976).
Kitagawa et al, *Biol. Pharm. Bull.*, 22(7):721-724 (1999).
Guo et al, *J. of Pharmacology and Exp. Therapeutics*, 289(1):448-454 (1999).
Tsuji et al, *J. of Pharmaceutical Sciences*, 79(12):1123-1124 (1990).
Ranaldi et al, *Antimicrogiol Agents and Chemotherapy*, 38(6):1239-1245 (1994).
Thwaites et al, *British J. of Pharmacology*, 115:761-766 (1995).
Oh et al, *J. of Pharmaceutical Sciences*, 91(12):2579-2587 (2002).
Barr et al, *J. of Pharmaceutical Sciences*, 59(2):154-163 (1970).
Yoshitomi, "Fundamental Experiment on Gastrointestinal Absorption", *Biopharmaceutics Experimental Manual*, Shigeru Goto (editor), Tokyo: Seishi Syoin, pp. 2-22 (1985).
Tamai, *J. of Pharmaceutical Society of Japan*, 117(7):415-434 (1997).
Tsuji, *Dai 122 Nenkai*, The Pharmaceutical Society of Japan Koen Yoshishu-1, The Pharmaceutical Society of Japan, p. 40 (2002).
Tamai, *Advances in Pharmaceutical Sciences*, 16:77-87 (2000).
Tamai, *Xenobiotic Metabolism and Disposition*, 14(2):158-170 (1999).
Sai et al, *Igaku no Ayumi*, 197(1):23-31 (2001).
DDS Gijutsu no Shinpo, Japan Technology Transfer Association et al, ISBN4-8407-1834-2, pp. 137-160 (1990).
Partial English Translation of Taiwanese Office Action pertaining to U.S. Appl. No. 10/541,019 dated Dec. 13, 2007; document found in U.S. Appl. No. 10/514,019, filed Apr. 10, 2013.

\* cited by examiner

GASTROINTESTINAL ABSORPTION ENHANCER MEDIATED BY PROTON-COUPLED TRANSPORTER AND ITS PREPARING METHOD

CROSS-REFERENCE TO RELATED APPLICATIONS

This is a divisional of application Ser. No. 11/971,243 filed Jan. 9, 2008, which is a divisional of application Ser. No. 10/541,019 filed Jun. 28, 2005, which in turn is a §371 National Stage entry of PCT/JP2004/00070, filed Jan. 8, 2004. The entire disclosure of the prior applications, application Ser. Nos. 11/971,243 and 10/541,019 and PCT/JP2004/00070, is hereby incorporated by reference.

TECHNICAL FIELD

The present invention relates to a gastrointestinal absorption enhancer mediated by a proton-coupled transporter and a method for preparing it.

BACKGROUND OF THE INVENTION

For many chronically diseased areas, oral administration is generally considered as a desirable route of pharmaceutical administration in view of convenience and cost. However, many candidate compounds for medicinal products exhibit low absorbability when administered orally since they have a low membrane permeability in the gastrointestinal tract or they are unstable therein, thereby facing a condition of being unable to maintain the blood concentration for sufficient pharmacological effects.

Moreover, it is known that there are some organic compounds that show a tendency of being barely absorbed although they are reported to be recognized by influx transporters expressed in small-intestinal epithelial cells (for example, Sakamato et al., *J. Antibiot.* 38 (1985): 496-504, and Kelly et al., *Clin. Pharmacokinet.* 19 (1990): 177-196, etc.).

Given this circumstance, research has been conducted in using various absorption enhancers and enzyme inhibitors to improve the absorption of compounds that are candidates for medical products. For example, Swenson et al., (*Adv. Drug Del. Rev.* 8 (1992): 39-92) and Kompella et al., (*Adv. Drug Del. Rev.* 46 (2001): 211-245) disclose methods for using absorption enhancers to improve peptide absorption. However, these methods pose the problem of cell damage by the absorption enhancers, which are primarily added to enhance absorption.

Hayakawa et al., (*Pharm. Res.* 9 (1992): 535-540) and Zhou et al., (*J. Control Rel.* 29 (1994): 239-252) teach methods for adding enzyme inhibitors to inhibit decomposition and promote absorption in the gastrointestinal tract. However, these methods cause problems such that no substrate specificity is obtained in absorption.

Furthermore, to improve absorption of furosemide, which is recognized by an efflux transporter in the gastrointestinal tract, addition of a pH-sensitive polymer is known (e.g., Terao et al. *J. Pharm. Pharmacol.* 53 (2000): 433-440). However, this reference does not suggest the use of transporters to improve gastrointestinal absorption, and has, as with the prior art methods described above, the problem of not imparting substrate specificity to gastrointestinal absorption.

In addition, there have been no prior art methods that enhance the absorption of organic compounds that are, despite being substrates for influx transporters, of poor absorbability.

DISCLOSURE OF THE INVENTION

An object of the invention is to provide a pharmaceutical preparation that can improve cellular absorption of a pharmaceutical composition and that can provide, through oral administration or like method, a blood concentration from which sufficient remedial effects can be expected, and to provide a method for producing such a preparation. Specifically, an object of the invention is to provide a pharmaceutical preparation having an excellent gastrointestinal absorbability comprising a compound recognized by a proton-coupled transporter and a pH-sensitive polymer in an amount sufficient to give a desirable pH at which the proton-coupled transporter optimally transports the compound into a cell in the gastrointestinal tract, and a production method thereof.

The inventors conducted extensive research to solve the aforementioned problems and found the facts described in (1) and (2) below:

(1) Compounds recognized by peptide transporters (hereinafter sometimes referred to as "substrates"), which is one type of the proton-coupled transporters, sometimes exhibit a tendency to be gastrointestinally poorly absorbed because the amount of protons ($H^+$), which are the driving force of peptide transporters for transporting substrates, is reduced as they travel to the lower gastrointestinal tract, and the ability of substrate transportation is thereby reduced; and (2) By adding a specific amount of pH-sensitive polymers to the substrate, the driving force of peptide transporters is increased and the gastrointestinal absorption of substrates having a tendency to be poorly absorbed is improved.

The inventors carried out further development based on these findings and found that cellular uptake of a substrate is most enhanced at the pH optimum for the proton-coupled transporter. The present invention was accomplished based on these findings.

In particular, the present invention provides the following:

Item 1. A pharmaceutical preparation exhibiting excellent gastrointestinal absorbability comprising a compound recognized by a proton-coupled transporter and a pH-sensitive polymer, the pH-sensitive polymer being used in an amount sufficient to impart the gastrointestinal tract a pH at which the proton-coupled transporter optimally functions for cellular uptake of the compound.

Item 2. A pharmaceutical preparation according to Item 1, wherein the proton-coupled transporter is an influx transporter expressed in a small-intestinal epithelial cell.

Item 3. A pharmaceutical preparation according to Item 2, wherein the proton-coupled transporter is one member selected from the group consisting of a peptide transporter, monocarboxylic acid transporter, and D-cycloserine-transporting amino acid transporter.

Item 4. A pharmaceutical preparation according to Item 3, wherein the proton-coupled transporter is a peptide transporter.

Item 5. A pharmaceutical preparation according to Item 4, wherein the compound recognized by the peptide transporter is at least one species selected from the group consisting of peptides, β-lactam antibiotics, angiotensin-converting enzyme inhibitors, antiviral agents, antitumor agents, and ω-amino carboxylic acids. ω

Item 6. A pharmaceutical preparation according to Item 3, wherein the proton-coupled transporter is a monocarboxylic acid transporter.

Item 7. A pharmaceutical preparation according to Item 6, wherein the compound recognized by the monocarboxylic acid transporter is at least one species selected from the group consisting of lactic acid, pyruvic acid, acetic acid, propionic acid, butyric acid, glycolic acid, nicotinic acid, salicylic acid, benzoic acid, p-aminobenzoic acid, and foscarnet.

Item 8. A pharmaceutical preparation according to Item 3, wherein the proton-coupled transporter is an amino acid transporter transporting D-cycloserine.

Item 9. A pharmaceutical preparation according to Item 8, wherein the compound recognized by the amino acid transporter transporting D-cycloserine is at least one species selected from the group consisting of L-alanine (α-alanine), β-alanine, L-proline, and glycin.

Item 10. A pharmaceutical preparation according to Item 1, wherein the pH at which the proton-coupled transporter optimally functions for cellular uptake of the compound is determined by evaluating under various pH conditions the extent of cellular uptake of the compound using cells in which the proton-coupled transporter is expressed.

Item 11. A pharmaceutical preparation according to Item 1, wherein the pH at which the proton-coupled transporter optimally functions for cellular uptake of the compound is determined by measuring the extent of the compound migrated within the gastrointestinal tract using the in situ closed loop method.

Item 12. A pharmaceutical preparation according to Item 1, wherein the pH-sensitive polymer is at least one species selected from the group consisting of dried methacrylic acid copolymer, methacrylic acid copolymer LD, methacrylic acid copolymer L, methacrylic acid copolymer S, polyacrylic acid, maleic acid/n-alkyl vinyl ether copolymer, hydroxypropylmethylcellulose acetate succinate, and hydroxypropylmethylcellulose phthalate.

Item 13. A pharmaceutical preparation according to Item 1, wherein the pH-sensitive polymer is at least one species selected from the group consisting of Eudragit L100-55, Eudragit 30D-55, Eudragit L100, Eudragit S100, Eudragit P-4135F, polyacrylic acid, maleic acid/n-alkyl vinyl ether copolymer, hydroxypropylmethylcellulose acetate succinate, and hydroxypropylmethylcellulose phthalate.

Item 14. A pharmaceutical preparation according to any of Items 1 to 13 that is used for oral administration.

Item 15. A method for formulating a pharmaceutical preparation having excellent gastrointestinal absorbability comprising the steps of:

(1) determining a pH at which the proton-coupled transporter optimally transports a compound recognized by the proton-coupled transporter into a cell; and (2) adding to the compound a pH-sensitive polymer in an amount sufficient to impart the pH optimum for cellular uptake of the compound.

Item 16. A pharmaceutical preparation formulated according to the method of Item 15.

Item 17. A pharmaceutical preparation for enhancing gastrointestinal absorbability of a compound recognized by a proton-coupled transporter, the pharmaceutical preparation comprising the compound and a pH-sensitive polymer in an amount sufficient for the gastrointestinal tract to acquire a pH at which the proton-coupled transporter optimally transports the compound into a cell.

Item 18. A method for enhancing gastrointestinal absorbability of a compound recognized by a proton-coupled transporter, the method comprising conditioning the gastrointestinal tract to a pH at which the proton-coupled transporter optimally transports the compound into a cell.

Item 19. A method for using a pH-sensitive polymer, to enhance gastrointestinal absorbability of a compound recognized by a proton-coupled transporter, in an amount sufficient to impart to the gastrointestinal tract a pH at which the proton-coupled transporter optimally transports the compound into a cell.

Item 20. Use of a pH-sensitive polymer, to enhance gastrointestinal absorbability of a compound recognized by a proton-coupled transporter, in an amount sufficient to impart to the gastrointestinal tract a pH at which the proton-coupled transporter optimally transports the compound into a cell.

Item 21. Use of a pH-sensitive polymer, for formulating a pharmaceutical preparation having an enhanced gastrointestinal absorbability of a compound recognized by a proton-coupled transporter, in an amount sufficient to impart to the gastrointestinal tract a pH at which the proton-coupled transporter optimally transports the compound into a cell.

DETAILED DESCRIPTION OF THE INVENTION

The present invention is directed to a pharmaceutical preparation exhibiting excellent gastrointestinal absorbability comprising a compound recognized by a proton-coupled transporter (substrate) and a pH-sensitive polymer. The pharmaceutical preparation comprises the pH-sensitive polymer in an amount sufficient for the gastrointestinal tract to acquire a pH at which the proton-coupled transporter optimally transports the substrate into a cell.

The present invention is described hereinbelow in more detail.

Proton-Coupled Transporters

The proton-coupled transporters of the invention refer to active transporters that transport substrates from the mammalian (especially, of humans) gastrointestinal tract into cells by taking advantage of the proton ($H^+$) gradient. Proton-coupled transporters are expressed within the gastrointestinal tract and the like, and, specifically, adjacent to the surface of the brush border membranes of the gastrointestinal tract (especially, the surface of the brush border membranes of small-intestinal epithelial cells). They are influx transporters actively transporting nutrients and medicaments into cells. The aforementioned small intestine includes the duodenum, jejunum and ileum.

Specific examples of proton-coupled transporters herein include peptide transporters (PEPT), monocarboxylic acid transporters, amino acid transporters transporting D-cycloserine, and the like.

The aforementioned peptide transporters (PEPT) serve to transport dipeptides, tripeptides, and similar compounds and contribute in a living body to absorbing proteins and maintaining peptidergic nitrogen sources. Specifically, examples thereof are peptide transporter 1 (PEPT1), which is composed of 710 amino acids and expressed mainly in the small intestine and kidney, and peptide transporter 2 (PEPT2), which is composed of 729 amino acids and expressed mainly in the kidney, brain, lung, spleen, etc.

Compounds absorbed into small-intestinal epithelial cells via influx transporters are further transported into the blood via basolateral peptide transporters present in the basolateral membranes of small-intestinal epithelial cells. Basolateral peptide transporters are facilitated diffusion transporters that serve to transport in accordance with the concentration gradient.

Monocarboxylic acid transporters transport lactic acid and contribute to maintenance of lactic acid, which is the final product of anaerobic glycolysis, in a living body.

Amino acid transporters transporting D-cycloserine transport amino acids and contribute to maintenance of amino acid in a living body.

Compounds Recognized by Proton-Coupled Transporters (Substrates)

Compounds recognized by proton-coupled transporters herein refer to compounds that can be recognized by the aforementioned proton-coupled transporters and taken up into cells (e.g., small-intestinal epithelial cells) from the gastrointestinal tract. Whether compounds can be recognized by the proton-coupled transporters or not is, for example, evaluated as follows:

The extent of cellular uptake of the compound is measured using cells in which a target proton-coupled transporter is expressed and cells in which no target transporter is expressed. When uptake into cells in which the target proton-coupled transporter is expressed is greater than in cells in which the transporter is not expressed, it is considered that the proton-coupled transporter is involved in the migration of the compound into the cells.

Cells in which a proton-coupled transporter is expressed herein denote those in which a proton-coupled transporter is endogenously expressed. Examples of cells endogenously expressing a proton-coupled transporter include Caco-2 cells, HT-29 cells, COLO-320 cells, HT-1080 cells, AsPc-1 cells, Capan-2 cells, SK-ChA-1 cells, etc.

Furthermore, using cells in which cellular uptake of the aforementioned compound has been observed, the aforementioned compound and another compound which is known to be recognized by a proton-coupled transporter (e.g., cefadroxil (CDX)) are simultaneously introduced to the test solutions, and cellular uptake of the former compound is then evaluated. If an inhibitory effect on the cellular uptake of the former compound is observed, this compound is considered to be recognized by the proton-coupled transporter.

The extent of cellular uptake of the compound can also be measured once cells in which a proton-coupled transporter is expressed are prepared. Such cells can be prepared according to known methods. For example, PEPT1 cDNA is incorporated into a mammalian cultured cell expression vector and an excessive amount of transporter is expressed in model cells (e.g., Hela cells) after transfection of the vector containing PEPT1 cDNA.

The extent of cellular uptake of a compound is evaluated, using cells in which a proton-coupled transporter is expressed and cells in which no proton-coupled transporter is expressed, by measuring the amount of the compound absorbed into cells per unit weight of cellular protein (the weight of the compound absorbed into cells relative to the total weight of protein contained in cells). For example, as for peptide transporters, it is evaluated using cells in which a proton-coupled transporter is expressed and cells in which no proton-coupled transporter is expressed, by measuring the amounts of the compound absorbed into cells per unit weight of cellular protein (μL/mg protein), comparing the amounts of the compound absorbed into transporter-expressed cells with those of transporter-unexpressed cells, and determining the extent of transporter absorption.

Among proton-coupled transporters, the aforementioned peptide transporters (PEPT) have broader substrate specificity than other nutrient transporters. Examples of compounds that are recognized by PEPT (especially by PEPT1) and absorbed into small-intestinal epithelial cells therefore include, in addition to peptides, β-lactam antibiotics, angiotensin-converting enzyme inhibitors, antiviral agents, antitumor agents, and ω-amino carboxylic acids, and a wide variety of other pharmaceutical compounds.

Specific examples of peptides are dipeptides and tripeptides. Dipeptides are not limited insofar as they are obtained by amide-coupling a pair of amino acids randomly selected from naturally- or synthetically-occurring amino acids. Preferable among these are glycylsarcosine, carnosine, lisinopril, etc. Tripeptides are not limited insofar as they are obtained by amide-coupling three amino acids randomly selected from naturally- or synthetically-occurring amino acids. Preferable examples among these are Phe-Cys-Val, Glu-His-Pro, Phe-Ala-Pro, etc.

Examples of β-lactam antibiotics include penicillin antibiotics, cephem antibiotics, and the like. Specific examples are amoxicillin, ampicillin, ciclacillin, phenoxymethylpenicillin, propicillin, carfecillin, carbenicillin, bacampicillin, pivampicillin, cefadroxil, cefixime, ceftibuten, cephaclor, cephalexin, cephradine, SCE-100, cefatrizine, cephalothin, cefdinir, loracarobef, FK089, latamoxef, pivcefalexine, cefazolin, cefoperazone, cefoxitin, cefotiam, cefinetazole, etc.

Examples of angiotensin-converting enzyme inhibitors include captopril, enalapril, quinapril, benazepril, fosinopril, lisinopril, SQ 29852, enalaprilat, quinaprilat, benazeprilat, fosinoprilat, and the like.

Examples of antiviral agents are valacyclovir and the like.
Examples of antitumor agents are bestatin and the like.
Examples of ω-amino carboxylic acids include compounds represented by General Formula (I):

$$H_2N-(CH_2)_n-COOH \qquad (1)$$

wherein n is an integer from 4 to 11.

Other examples are L-dopa-L-phenylalanine, 4-aminophenyl acetic acid (4-APAA), δ-aminolevulinic acid (ALA), etc.

Examples of compounds recognized by the aforementioned monocarboxylic acid transporters of proton-coupled transporters and absorbed into cells include lactic acid, pyruvic acid, acetic acid, propionic acid, butyric acid, glycolic acid, nicotinic acid, salicylic acid, benzoic acid, p-aminobenzoic acid, foscarnet, etc.

Examples of compounds recognized by the aforementioned D-cycloserine-transporting amino-acid transporters of proton-coupled transporters and absorbed into cells include L-alanine, β-alanine, L-proline, glycine, etc.

pH Profiles of Substrates

The pH profile of a compound recognized by a proton-coupled transporter (substrate) herein refers to the characteristics of cellular uptake of the substrate effected by a proton-coupled transporter under varying pH conditions (characteristics of cellular absorption depending on pH conditions). Based on the pH profile, the optimum pH can be obtained for a specific proton-coupled transporter to transport a specific substrate into cells.

The extent of cellular uptake of a substrate under various pH conditions (the amount of substrate absorption into cells) can be measured as follows: Using cells in which a proton-coupled transporter is expressed, the extent of cellular uptake of a substrate is measured in vitro under various pH conditions. For example, the pH profile of substrates recognized by PEPT1 can be obtained by measuring in vitro under various pH conditions (e.g., pHs from about 5.4 to about 7.5) the extent of cellular uptake of the substrates, using cells expressing PEPT1 such as human colon cancer-derived Caco-2 cells, which are gastrointestinal tract model cells.

Specifically, measurement can be conducted according to a method already reported (Tsuji, A., Takanaga, H., Tamai, I., and Terasaki, T. "Transcellular Transport of Benzoic Acid Across Caco-2 Cells by a pH-Dependent and Carrier-Mediated Transport Mechanism". Pharm. Res. 11 (1994): 30-37. (see, for example, Example 1)

Cellular absorption in vitro can be a guideline for evaluating in vivo membrane permeability in the gastrointestinal tract. The pH of the gastrointestinal tract in humans under physiological conditions is reported to be 5.4 to 7.5 (Davies, B., and Morris, T. "Physiological Parameters in Laboratory Animals and Humans". *Pharm. Res.* 10 (1993): 1093-1095). Absorption in the gastrointestinal tract in vivo is therefore considered to occur under these pH conditions.

The extent of cellular uptake of a substrate under various pH conditions can also be estimated by measuring the amount of the substrate absorbed into the gastrointestinal tract under various pH conditions using a rat gastrointestinal tract loop, e.g., intestinal loop (in situ closed loop method). When a rat gastrointestinal tract loop is used, the measurement can be conducted in reference to the following reports: Barr, W. H., and Riegelman, S. "Intestinal Drug Absorption and Metabolism I. Comparison of Methods and Models to Study Physiological Factors of In Vitro and In Vivo Intestinal Absorption". *J. Pharm. Sci.* 59 (1970): 154-163; and Hironori Yoshitomi. "Fundamental Experiment on Gastrointestinal Absorption". *Biopharmaceutics Experimental Manual*. Shigeru Goto (editor). Tokyo: Seishi Syoin, 1985: 2-22.

For example, rats are anesthetized by intraperitoneally administering pentobarbital sodium (50 mg/kg). Then, laparotomy is performed along the median line to expose the intestinal tract, and a loop is formed at the ileum (e.g., FIG. 6). MES buffer containing medical fluid and a polymer (5 mM KCl, 100 mM NaCl, 10 mM 2-(N-morpholino)ethanesulfonic acid (MES), 85 mM mannitol, 0.01% polyethylene glycol; pH 6.0; osmotic pressure 290 mOs/kg) is introduced into the intestinal loop and both ends of the loop are ligated. Subsequently, the intestinal loop is immediately returned to the abdominal cavity. An incandescent lamp is used to maintain the body temperature. The solution inside the intestinal loop is retrieved 20 minutes after its administration. The pH was measured by pH-meter. The amount of medicaments are measured by HPLC.

In addition, the pH profile of substrates recognized by PEPT1 can be obtained by measuring the uptake into oocytes under various pH conditions once cRNA hPEPT1 is injected into *X. laevis* oocytes. Alternatively, the pH profile can be measured using an electrophysiological method by detecting the electric potential difference generated upon adding substrates for peptide transporters.

Specifically, the measurement can be conducted in reference to the method described in "Expression Cloning of a Mammalian Proton-Coupled Oligopeptide Transporter" by Fei, Y. J., Kanai, Y., Nussberger, S., Ganaphthy, V., Leibach, F. H., Romero, M. F., Singh, S. K., Boron, W. F., and Hediger, M. A., *Nature* 368 (1994): 563-566.

Generally, although the optimum pH for uptake of substrates in the gastrointestinal tract varies according to the target proton-coupled transporters and types of substrates, a pH profile obtained according to the aforementioned methods shows the extent of cellular uptake of substrates recognized by the proton-coupled transporters under various pH conditions, thereby enabling the "pH of the proton-coupled transporters optimum for cellular uptake of substrates" to be determined.

pH-Sensitive Polymers pH-sensitive polymers herein refer to those that release protons depending upon the pH of the specific site of a living body (e.g., gastrointestinal tract), for example, polymers that dissolve or swell by releasing protons under high pH conditions. By using a specific amount of this pH-sensitive polymer in combination with a substrate, the pH of the gastrointestinal tract (in particular, sites adjacent to the surface of the brush border membranes of the gastrointestinal tract) can be controlled to be optimum for cellular uptake of a substrate recognized by the proton-coupled transporter.

Specific examples include dried methacrylic acid copolymers, methacrylic acid copolymers LD, methacrylic acid copolymers L, methacrylic acid copolymers S, polyacrylic acids, maleic acid/n-alkyl vinyl ether copolymers, hydroxypropylmethylcellulose acetate succinates, hydroxypropylmethylcellulose phthalates, etc. More specifically, examples are Eudragit L100-55 (Eudragit is a registered trademark, same applies hereinbelow), Eudragit 30D-55, Eudragit L100, Eudragit S100, Eudragit P-4135F, and the like. Those commercially available and those prepared according to known methods can be used as these pH-sensitive polymers.

Among these pH-sensitive polymers, preferably used in the pharmaceutical preparation of the present invention are, for example, Eudragit L100-55, Eudragit L100, Eudragit S100, Eudragit P-4135F, and the like, and particularly preferable are Eudragit L100-55 and Eudragit L100.

Pharmaceutical Preparations

The pharmaceutical preparation of the invention is formulated by mixing, with a compound recognized by a proton-coupled transporter, a pH-sensitive polymer in an amount sufficient for imparting the pH optimum for cellular uptake of the compound in the gastrointestinal tract based on the pH profile of the compound. The phrase "in the gastrointestinal tract" as used above refers, for example, to "in the small intestine". It refers particularly to "at sites adjacent to the surface of the brush border membranes of the gastrointestinal tract", and more particularly to "at the surface of the brush border membranes of small-intestinal epithelial cells where proton-coupled transporters are expressed, and in locations adjacent thereto".

The amount of pH-sensitive polymer to be used can be determined, for example, through experiments so as to obtain the desired extent of substrate absorption. Specifically, the amount of pH-sensitive polymer to obtain the desired extent of substrate absorption can be determined by altering the amounts of pH-sensitive polymer added to the substrate using the in situ closed loop method or oral-administration in rats (see, for example, Example 3).

The amount of pH-sensitive polymer used in the pharmaceutical preparation of the invention, although it varies according to the property of a substrate, may be, for example, about 1 to about 1000 parts by weight, preferably about 50 to about 500 parts by weight, and more preferably about 100 to about 300 parts by weight, per part by weight of substrate. Alternatively, the amount of pH-sensitive polymer may be about 5 to about 40 wt. %, and preferably about 10 to about 20 wt. %, based on the weight of the entire pharmaceutical preparation.

Preferable embodiments of the pharmaceutical preparation of the present invention containing a compound recognized by a proton-coupled transporter and a pH-sensitive polymer include preparations containing a dipeptide and methacrylic acid copolymer, preparations containing a β-lactam antibiotic and methacrylic acid copolymer, etc.

With regard to preparations containing a dipeptide and a methacrylic acid copolymer, specific examples of the dipeptide are glycylsarcosine, carnosine, lisinopril, etc. Specific examples of the methacrylic acid copolymer are dried methacrylic acid copolymers (e.g., Eudragit L100-55), methacrylic acid copolymers LD (e.g., Eudragit 30D-55), methacrylic acid copolymers L (e.g., Eudragit L100), methacrylic acid copolymers S (e.g., Eudragit S100), etc. An especially preferable embodiment include those containing glycylsarcosine or carnosine, and Eudragit L100-55.

With regard to preparations containing a β-lactam antibiotic and a methacrylic acid copolymer, examples of the β-lactam antibiotic include penicillin antibiotics, cephem antibiotics, and the like. Specific examples are amoxicillin, ampicillin, ciclacillin, phenoxy-methylpenicillin, propicillin, carfecillin, carbenicillin, bacampicillin, pivampicillin, cefadroxil, cefixime, ceftibuten, cephaclor, cephalexin, cephradine, SCE-100, cefatrizine, cephalothin, cefdinir, loracarobef, FK089, latamoxef, pivcefalexine, cefazolin, cefoperazone, cefoxitin, cefotiam, cefinetazole, etc. Specific examples of the methacrylic acid copolymer are as described above. An especially preferable embodiment includes those containing cefadroxil, cefixime, or FK089, and Eudragit L100-55.

The pharmaceutical preparation of the invention comprises a compound recognized by the aforementioned proton-coupled transporter (substrate) and a specific amount of a pH-sensitive polymer, and can be orally administered to mammals (especially humans) as it is as a powdered medicine. The pharmaceutical preparation can also be administered having been formulated according to various methods. For example, it can be administered as tablets, granules, capsules, suppositories, and enemas. The pharmaceutical preparation in these forms can contain, as necessary, excipients, disintegrants, lubricants, and various other additives known in pharmaceutical production.

In particular, it is preferable to formulate an enteric, sustained-release pharmaceutical preparation or the like that can deliver the medicament and pH-sensitive polymer throughout the gastrointestinal tract. Furthermore, the pharmaceutical preparation can be formulated into a liquid form (such as solution, suspension, syrup, and the like) containing the medicament and pH-sensitive polymer, thereby, compared with conventional tablets, enabling more thorough delivery of the medicament and pH-sensitive polymer, due to its water content, throughout the gastrointestinal tract. The pharmaceutical preparation can be formulated into these forms according to known methods.

The pharmaceutical preparation of the invention enhances the absorbability of a compound recognized by a proton-coupled transporter in the gastrointestinal tract because the gastrointestinal tract is conditioned by the pH-sensitive polymer contained therein to the pH optimum for cellular uptake of the compound. In particular, since the pharmaceutical preparation of the invention contains a pH-sensitive polymer in an amount sufficient to maintain the pH optimum for cellular uptake, medicament (substrate) can be readily absorbed even in the lower gastrointestinal tract (ileum and so on) where the amount of protons is decreased, and thereby a decrease in transporting ability of proton-coupled transporters is inhibited. Hence, the pharmaceutical preparation of the invention, even when administered orally, can provide a sufficient blood concentration of a medicament and achieve high bioavailability. Incidentally, the pH-sensitive polymer temporarily controls the pH of the gastrointestinal tract and does not adversely affect the gastrointestinal tract. The phrase "the pH-sensitive polymer temporarily controls the pH" means that the pH of a site where a substrate is absorbed into cells is impermanently controlled for an amount of time necessary for the cellular absorption of the substrate to complete.

BEST MODE FOR CARRYING OUT THE INVENTION

Examples are given below to illustrate the invention in more detail, but the scope of the invention is not limited to these examples.

Example 1

To investigate the effect of extracellular fluid on the cellular uptake of dipeptides and β-lactam antibiotics transported by PEPT1, the cellular uptake of dipeptides, i.e., [$^{14}$C]glycylsarcosine ([$^{14}$C]GlySar) and [$^{3}$H]carnosine, and β-lactam antibiotics, i.e., cefadroxil (CDX), cefixime (CFIX), and FK089, was evaluated at pH 5.0 to 7.0 using gastrointestinal tract model cells (Caco-2 cells).

Cells cultured on 4-well plates were rinsed 3 times with 1 mL Hanks' balanced salt solution (HBSS: 0.952 mM $CaCl_2$, 5.36 mM KCl, 0.441 mM $KH_2PO_4$, 0.812 mM $MgSO_4$, 136.7 mM NaCl, 0.385 mM $Na_2HPO_4$, 25 mM D-glucose, 10 mM HEPES; pH 7.4; osmotic pressure 315 mOs/kg) heated to 37° C., and uptake was initiated by adding 250 µL HBSS containing medical fluid. Uptake was terminated at a predetermined period of time by washing the cells 3 times with 1 mL ice-cooled HBSS. After the completion of uptake, 0.25 mL 5 N NaOH was added, and the cells were agitated for 2 hours to solubilize, followed by neutralization with 0.25 mL 5 N HCl. The medicaments contained in the solution extracted from the cells were quantified by a liquid scintillation counter or liquid chromatography (HPLC). Proteins contained in the cells were quantified using a protein assay kit (Bio-Rad, Richmond, Calif., USA) according to the Bradford assay (Bradford, M. M. "A Rapid and Sensitive Method for the Quantitation of Microgram Quantities of Protein Utilizing the Principle of Protein-Dye Binding". *Anal. Biochem.* 72 (1976): 248-254).

Figure 1A:
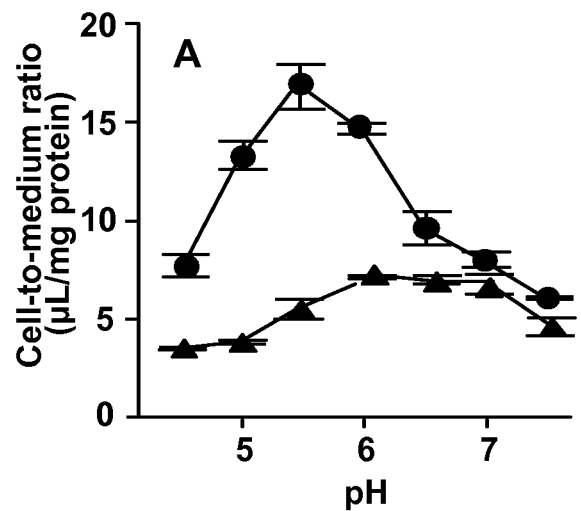
FIG. 1A is a graph showing the extent of cellular uptake of dipeptides into Caco-2 cells under various pH conditions (pH profile).
Figure 1B:
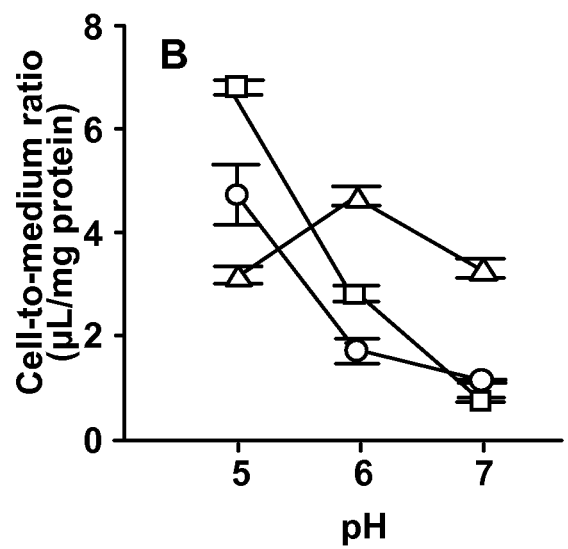
FIG. 1B is a graph showing the extent of cellular uptake of β-lactam antibiotics into Caco-2 cells under various pH conditions (pH profile).

FIGS. 1A and 1B show the effect of pH upon the uptake of the aforementioned dipeptides and β-lactam antibiotics into Caco-2 cells.

FIG. 1A shows the extent of uptake over 5 minutes, under different pH conditions, of 10 µM [$^{14}$C]GlySar (●) and 0.15 M [$^{3}$H] carnosine (▲) into Caco-2 cells at a temperature of 37° C. Each plot represents the mean±standard error of 3 to 4 experiments.

As shown in FIG. 1A, the uptake of [$^{14}$C]GlySar is clearly pH-dependent. The greatest uptake was observed between pH 5.0 and 6.0. On the other hand, FIG. 1A shows that the uptake of [$^{3}$H] carnosine, which is cationic in the weakly acidic region, was significant between pH 6.0 and 7.0. That is, the results demonstrated that the optimum pHs for [$^{14}$C]GlySar and [$^{3}$H] carnosine uptake are different.

FIG. 1B shows the results of measuring the uptake of 2 mM CFIX (□), 2 mM FK089 (○), and 2 mM CDX (∆) over 15 minutes. Each plot represents the mean±standard error of 3 to 4 experiments.

As with the dipeptides, FIG. 1B shows that the uptake of β-lactam antibiotics into Caco-2 cells is significantly pH-dependent, and that when the pH of the extracellular fluid is decreased from 6.0 to 5.0 the cellular uptake of anionic β-lactam antibiotics CFIX and FK-089 was greatly enhanced. In contrast, the optimum uptake of CDX, which is a zwitterionic β-lactam antibiotic at physiological pH, was observed at pH 6.0.

Example 2

To investigate whether it is possible to control pH by adding pH-sensitive polymers, the effect of such a polymer on the pH of MES buffer was examined.

A methacrylic acid copolymer (Eudragit L100-55) was used as a pH-sensitive polymer, and an aminoalkyl/methacrylate copolymer (Eudragit RS PO) was used as a pH-insensitive polymer.

A polymer (methacrylic acid copolymer Eudragit L100-55 or, of a pH-insensitive polymer, aminoalkyl/methacrylate copolymer Eudragit RS PO) was added to MES buffer (pH 6.0). Subsequently, the pH of the buffer was measured by a pH meter.

Figure 2:
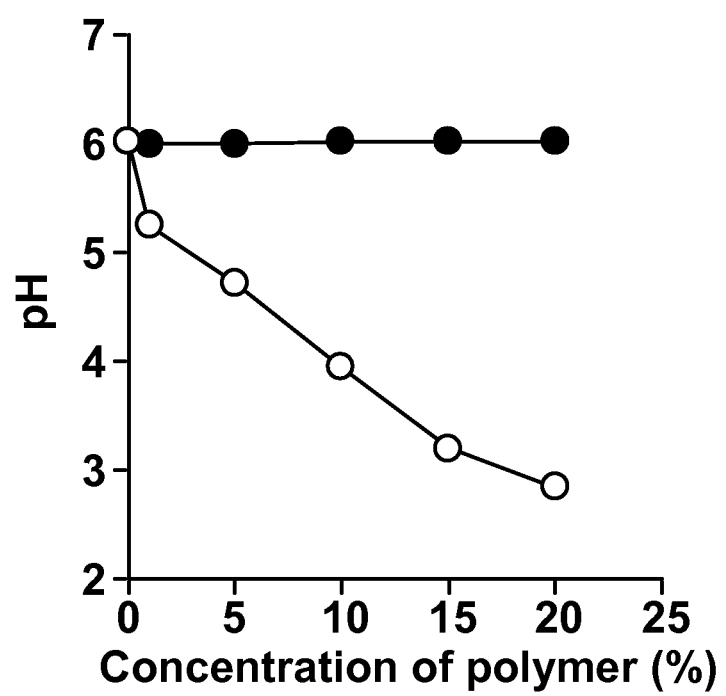
FIG. 2 is a graph showing the effect of an acidic polymer on the pH of MES buffer.

The pH of the buffer decreased as Eudragit L100-55 was added (FIG. 2). In FIG. 2, plots (●) represent the pH of the MES buffer containing Eudragit RS PO, and plots (○) represent the pH of the MES buffer containing Eudragit L100-55. Compared with the pH of the buffer having no polymer content, pH was decreased to about 3.0 when Eudragit L100-55 was added to a proportion of 20%. In contrast, the use of Eudragit RS PO, which has no proton-dissociating groups in its structure, did not result in a significant decrease in pH.

Example 3

Figure 6:
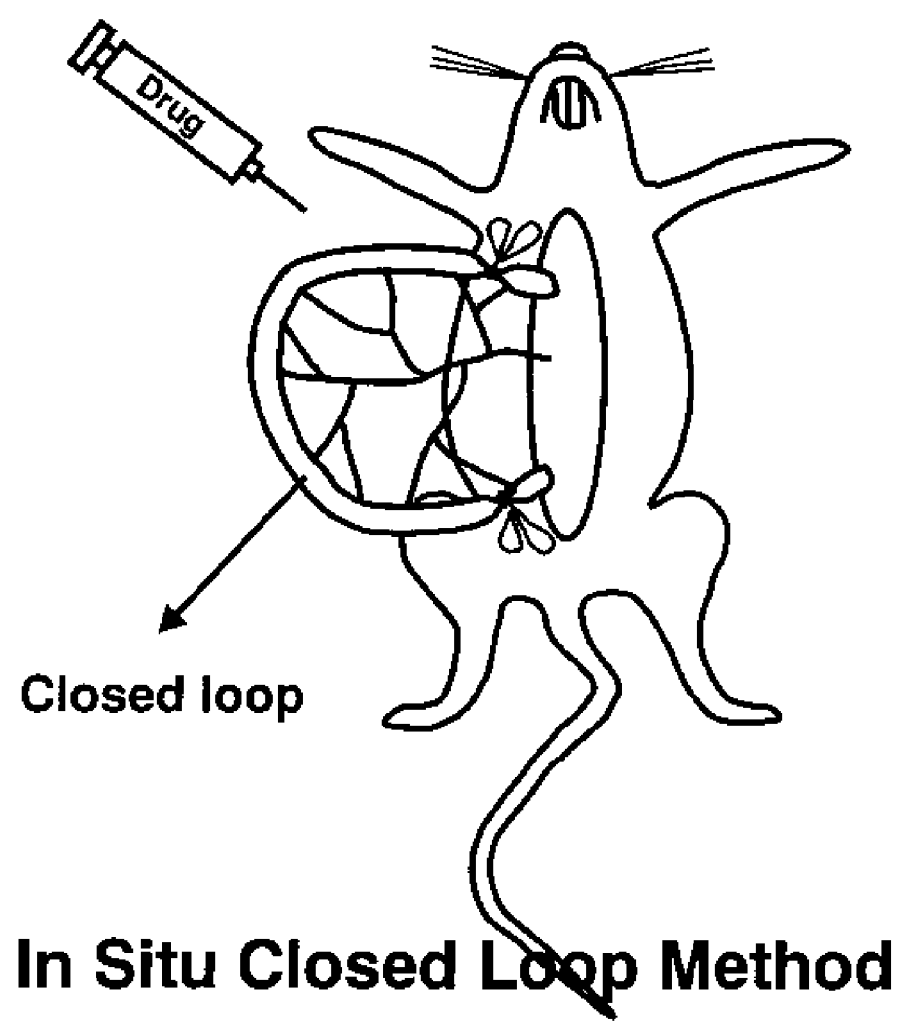
FIG. 6 depicts an intestinal loop used in the in situ closed loop method.

To investigate whether gastrointestinal absorption in rats of β-lactam antibiotics under physiological conditions can be improved by controlling the gastrointestinal pH, absorption of a zwitterionic compound (CDX) and an anionic compound (CFIX) in the presence and absence of a pH-sensitive polymer (Eudragit L100-55) was examined using the in situ closed loop method (FIG. 6 shows a diagram).

The oral composition of the invention was prepared by adding a β-lactam antibiotic (CDX or CFIX) to 10 mM MES buffer (pH 6.0) such that the buffer contained CDX in an amount of 1 mM or CFIX in an amount of 0.5 mM, and further adding Eudragit L100-55 to the buffer so that it contained in a proportion of 10 or 20 wt. % based on the amount of the entire oral composition. A β-lactam antibiotic solution containing no Eudragit L100-55 was prepared as a control.

These compositions were administered into the intestinal loops prepared at the caecum junction of SD male rats (junction between the terminal of the ileum and where the caecum starts) to a distance of 14 cm toward the stomach. The solution remaining in the intestinal loops was retrieved 20 minutes after administration. The concentration of β-lactam antibiotic in the retrieved solution was measured by HPLC, and pH of the retrieved solution was measured using a pH meter. Absorbability was evaluated according to the decrease in the concentration of β-lactam antibiotic in the retrieved solution in comparison with the concentration thereof in the solution administered.

Figure 3:
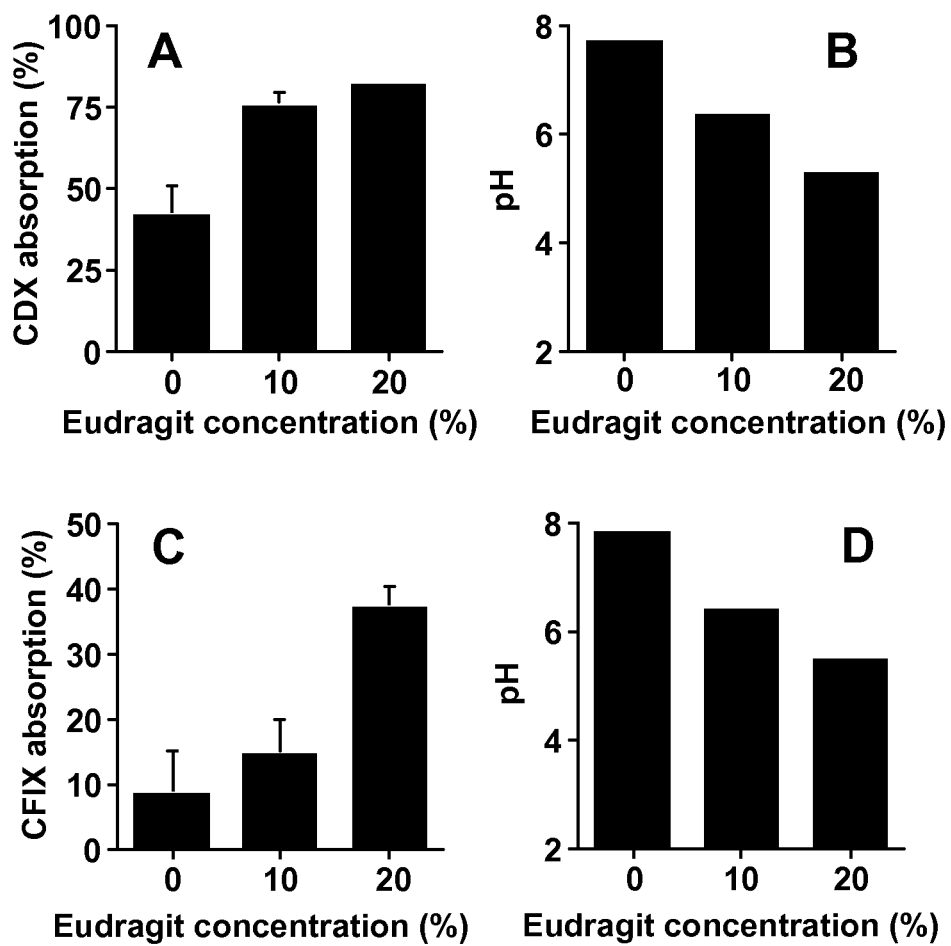
FIG. 3 is graphs showing absorption and pH in the lower small intestine of rats when a β-lactam antibiotic (CDX or CFIX) is used in combination with Eudragit L100-55.

As shown in FIG. 3A, absorption of CDX containing no Eudragit L100-55 was about 40%. However, significant increase was observed from the use of Eudragit L100-55 in a proportion of 20 wt. %, resulting in CDX absorption of about 80%. Moreover, gastrointestinal pH decreased as Eudragit L100-55 was added (FIG. 3B).

In contrast, CFIX was hardly absorbed by the rat ileum (FIG. 3C). However, as with CDX, the use of Eudragit L100-55 in a proportion of 20 wt. % significantly improved CFIX absorption to about 35%. The pH of the fluid in the gastrointestinal tract was decreased by Eudragit L100-55 (FIG. 3D).

Example 4

To investigate whether absorption of orally-administered peptidergic compounds in rats is improved by controlling gastrointestinal pH using pH-sensitive polymers, the time course of the plasma concentration of CFIX was examined after orally administering the peptidergic compound CFIX in combination with a pH-sensitive polymer (Eudragit L100-55) or pH-insensitive polymer (Eudragit RS PO).

The oral composition of the invention was prepared by adding Eudragit L100-55 to an aqueous solution of CFIX (0.23 mg/mL) such that the solution contained Eudragit L100-55 in a proportion of 5 wt. % based on the amount of the entire oral composition. A CFIX solution containing no Eudragit L100-55 was prepared as a control. These compositions were orally administered to SD male rats (body weight: 190 to 220 g) fasted for an entire day and night such that CFIX was given in a dose of 2.3 mg/kg. Blood was collected 15 to 480 minutes after administration, and the plasma concentration of CFIX was measured by HPLC. Based on the plasma concentration profile of CFIX thus obtained, the area under the plasma drug concentration-time curve (AUC) and highest drug concentration observed in plasma following administration of an extravascular dose (Cmax) were obtained.

Figure 4:
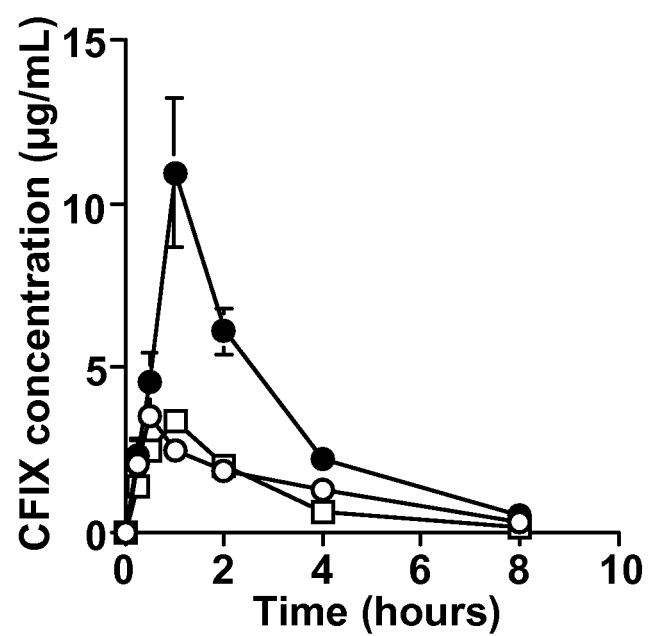
FIG. 4 is a graph showing the time course of blood concentration after orally administering CFIX and a polymer into rats.

FIG. 4 shows the absorption profile of CFIX after orally administering the composition into rats (CFIX: 2.3 mg/kg). Plots (○) represent absorption of CFIX in the absence of a polymer, plots (●) represent absorption of CFIX in the presence of Eudragit L100-55 (500 mg/kg), and plots (□) represent absorption of CFIX in the presence of Eudragit RS PO (500 mg/kg). Each plot represents the mean±standard error of 5 experiments.

As shown in Table 1, when CFIX and Eudragit RS PO as a pH-insensitive polymer were administered simultaneously, no meaningful differences from the administration of CIFX alone were observed in blood concentration-time curve area under the plasma drug concentration-time curve (AUC), maximum plasma drug concentration highest drug concentration observed in plasma following administration of an extravascular dose (Cmax), or time at which the highest drug concentration occurs following administration of extravascular dose (Tmax). Also, no change was observed in absorption of orally-administered CFIX.

However, when CFIX and pH-sensitive acidic Eudragit L100-55 were simultaneously administered, significant increases were observed in AUC and Cmax compared with the control containing no polymer, resulting in substantial increase in absorption of orally-administered CFIX.

Example 5

Figure 5:
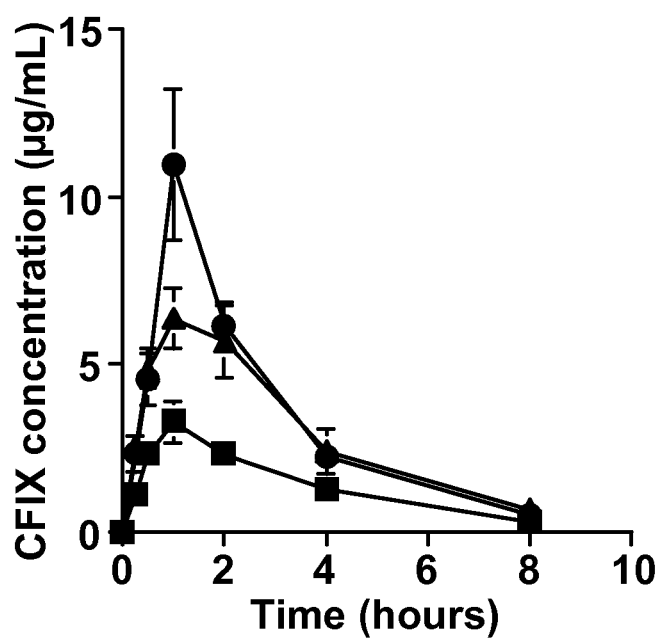
FIG. 5 is a graph showing the time course of CFIX blood concentration after orally administering CFIX, Eudragit L100-55 and CDX into rats.

To investigate whether the effect of the pH-sensitive acidic polymer enhancing CFIX absorption as shown in Example 4 was mediated by a peptide transporter (PEPT1) expressed in small-intestinal epithelial cells, the effect of CDX, which is a substrate for PEPT1, upon CFIX absorption was examined after orally administering CFIX and CDX simultaneously (FIG. 5 and Table 1).

The experimental procedure was as described in Example 4 except that CDX was simultaneously administered.

FIG. 5 depicts the influence of CDX on the oral administration profile of CFIX after administering the composition (CFIX: 2.3 mg/kg) to rats. Plots (●) represent absorption of CFIX when Eudragit L100-55 (500 mg/kg) and 0 mM CDX were used, plots (▲) represent absorption of CFIX when Eudragit L100-55 (500 mg/kg) and 2 mM CDX were used, and plots (■) represent absorption of CFIX when Eudragit L100-55 (500 mg/kg) and 10 mM CDX were used. Each plot represents the mean±standard error of 5 experiments.

As shown in FIG. 5 and Table 1, when Eudragit L100-55 and 2 mM CDX were administered simultaneously, although no significant differences were observed in AUC of CFIX compared with the administration of Eudragit L100-55 without CDX, Cmax was significantly decreased. Moreover, when CDX was administered in an amount of 10 mM, both AUC and Cmax of CFIX were significantly decreased.

As demonstrated above, absorption performed by the peptide transporter is considered to be involved in the improvement of CFIX absorption attained by the use of Eudragit L100-55.

Table 1 shows the pharmacokinetic parameters calculated based on the data points shown in FIGS. 4 and 5 representing the time course of blood concentrations.

TABLE 1

| Sample | $AUC_{0-8h}$ (μg · hr/mL) | Cmax (μg/mL) | Tmax (hr) |
|---|---|---|---|
| Control | 10.81 ± 1.48 | 4.13 ± 0.50 | 0.72 ± 0.20 |
| Eudragit L100-55 | 27.60 ± 2.39$^a$ | 11.52 ± 1.86$^a$ | 1.20 ± 0.20 |
| Eudragit L100-55 + CDX 2 mM | 24.24 ± 4.20 | 6.39 ± 0.88$^b$ | 1.00 ± 0.00 |
| Eudragit L100-55 + CDX 10 mM | 11.52 ± 0.99$^b$ | 3.40 ± 0.60$^b$ | 1.43 ± 0.20 |
| Eudragit RS PO | 8.83 ± 0.28 | 3.39 ± 0.16 | 1.00 ± 0.00 |

Each data represents the mean ± S.E.M. of three experiments at least.
$^a$Significantly different from the corresponding control value at $p < 0.05$.
$^b$Significantly different from the corresponding Eudragit L100-55 values at $p < 0.05$.

All the references cited in this specification are incorporated herein by reference.

EFFECTS OF THE INVENTION

The pharmaceutical preparation of the present invention has been completed based on the finding that cellular uptake of a substrate is enhanced most at the optimum pH for a proton-coupled transporter. The pharmaceutical preparation of the invention, therefore, is prepared, in view of the optimum pH of a proton-coupled transporter for cellular uptake of a substrate, by adding a pH-sensitive polymer in an amount sufficient for attaining such pH.

Hence, the pharmaceutical preparation of the invention dramatically improves absorption of pharmaceutical compounds in the gastrointestinal tract and achieves, through oral administration or like method, high blood concentration from which sufficient remedial effects are expected.

Furthermore, the pharmaceutical preparation imparts high absorbability throughout the entire gastrointestinal tract even to compounds recognized by proton-coupled transporters that have been known to be of poor absorbability.

Thus, the pharmaceutical preparation of the invention has a pharmaceutically remarkable property that it can effectively improve the remedial effects of oral administrations or like methods with low doses.

The invention claimed is:

1. A method for using a pH-sensitive polymer comprising:
   measuring a pH at which a peptide transporter 1 optimally transports a compound recognized by the peptide transporter 1 into a cell,
   mixing the compound and the pH-sensitive polymer, and
   adjusting a pH of a small intestinal tract to the previously measured pH by introducing the mixture to the small intestinal tract, thereby enhancing small intestinal absorbability of the compound
   wherein the pH-sensitive polymer is at least one member selected from the group consisting of dried methacrylic acid copolymer, methacrylic acid copolymer LD, methacrylic acid copolymer L, methacrylic acid copolymer S, polyacrylic acid, maleic acid/n-alkyl vinyl ether copolymer, hydroxypropylmethylcellulose acetate succinate, and hydroxypropylmethylcellulose phthalate, and
   wherein the amount of the pH-sensitive polymer is about 50 to about 1000 parts by weight per part by weight of the compound recognized by the peptide transporter 1.

2. The method for using a pH-sensitive polymer according to claim 1, wherein the compound recognized by the peptide transporter 1 is at least one member selected from the group consisting of peptides, β-lactam antibiotics, angiotensin-converting enzyme inhibitors, antiviral agents, antitumor agents, and ω-amino carboxylic acids.

3. The method for using a pH-sensitive polymer according to claim 1 further comprising measuring the pH at which the peptide transporter 1 optimally transports by evaluating under various pH conditions the extent of cellular uptake of the compound using cells in which the peptide transporter 1 is expressed.

4. The method for using a pH-sensitive polymer according to claim 1 further comprising measuring the pH at which the peptide transporter 1 optimally transports by measuring the extent of the compound migrated within the small intestinal tract using the in situ closed loop method conducted in the intestinal tract.

* * * * *